(12) United States Patent
Jugl et al.

(10) Patent No.: US 9,067,018 B2
(45) Date of Patent: Jun. 30, 2015

(54) CARTRIDGE HOLDER ASSEMBLY FOR A DRUG DELIVERY DEVICE

(75) Inventors: Michael Jugl, Frankfurt am Main (DE); Gunther Sendatzki, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 389 days.

(21) Appl. No.: 13/501,183

(22) PCT Filed: Oct. 14, 2010

(86) PCT No.: PCT/EP2010/065444
§ 371 (c)(1),
(2), (4) Date: Oct. 12, 2012

(87) PCT Pub. No.: WO2011/054648
PCT Pub. Date: May 12, 2011

(65) Prior Publication Data
US 2013/0030378 A1    Jan. 31, 2013

(30) Foreign Application Priority Data

Oct. 16, 2009 (EP) ..................................... 09173305

(51) Int. Cl.
*A61M 5/315* (2006.01)
*A61M 5/24* (2006.01)
*A61M 5/31* (2006.01)

(52) U.S. Cl.
CPC ............. *A61M 5/24* (2013.01); *Y10T 29/49826* (2015.01); *A61M 5/2466* (2013.01); *A61M 5/3134* (2013.01); *A61M 5/31573* (2013.01); *A61M 2005/2407* (2013.01)

(58) Field of Classification Search
CPC ............................. A61M 5/24; A61M 5/3134
USPC .......................... 604/246, 219, 207, 206, 211
See application file for complete search history.

(56) References Cited

U.S. PATENT DOCUMENTS

| 3,557,787 A | 1/1971 | Cohen |
| 3,682,174 A | 8/1972 | Cohen |
| 3,757,779 A | 9/1973 | Rovinski |
| 5,616,135 A | 4/1997 | Thorne et al. |
| 5,810,778 A * | 9/1998 | Hjertman ...................... 604/143 |

FOREIGN PATENT DOCUMENTS

| WO | 00/53241 | 9/2000 |
| WO | 00/53241 A2 | 9/2000 |
| WO | 2006/063124 | 6/2006 |
| WO | 2006/063124 A2 | 6/2006 |
| WO | 2007/017053 | 2/2007 |
| WO | 2007/017053 A1 | 2/2007 |
| WO | 2008/145171 | 12/2008 |
| WO | 2008/145171 A1 | 12/2008 |

OTHER PUBLICATIONS

Form PCT/IB/328, Notification Concerning Transmittal of Copy of International Preliminary Report on Patentability.

* cited by examiner

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

The present invention relates to a cartridge holder assembly for a drug delivery device as well as to such drug delivery device and to a corresponding method of assembly, wherein the cartridge holder assembly comprises:
a cartridge holder (14; 40) adapted to receive a cartridge (12) to be filled with a medicinal product to be dispensed by the drug delivery device, wherein the cartridge holder (14; 40) comprises at least one through opening at a distal end section to receive a piercing element (20) being adapted to penetrate a sealing septum (22) of the cartridge (12),
a constriction member (26; 42) being adapted to axially abut against the septum (22) and comprising a through opening (34; 52) to receive the piercing element (20), wherein said through opening (34; 52) is adjustable in diameter.

12 Claims, 7 Drawing Sheets

CARTRIDGE HOLDER ASSEMBLY FOR A DRUG DELIVERY DEVICE

CROSS REFERENCE TO RELATED APPLICATIONS

The present application is a 35 U.S.C. 371 National Application of PCT/EP2010/065444 filed Oct. 14, 2010, which claims priority to European Patent Application No. 09173305.5, filed Oct. 16, 2009, the entire contents of which are incorporated entirely herein by reference.

FIELD OF THE INVENTION

The present invention relates to drug delivery devices and in particular to pen-type injectors, that is to injectors of the kind that provide for administration by injection of medicinal products from a multidose cartridge. In particular, the present invention relates to such injectors, where a user may set and dispense the dose.

BACKGROUND AND PRIOR ART

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, such devices have to fulfill a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reducible, the device should be inexpensive to manufacture and easy to dispose. Moreover, the device should be suitable for recycling. To meet these requirements, the number of parts required to assemble the device and the number of material types the device is made from need to be kept to a minimum.

The medicinal product to be dispensed by means of the drug delivery device is typically provided in a disposable or replaceable cartridge, such as a vial, ampoule or carpule comprising a slidably disposed piston to be operably engaged with a piston rod of the drug delivery device's drive mechanism. By applying thrust to the cartridge's piston in distal direction, a predefined dose of the liquid drug can be dispensed and expelled from the cartridge.

Cartridges as they are typically used with drug delivery devices, such as pen-type injectors are typically sealed by means of as sealing septum. Such a septum is commonly designed as rubber stopper providing an air-tight seal but being pierceable by piercing elements such as needles or cannulae.

A typical cartridge holder assembly 10 as known in the prior art is illustrated in cross section in FIG. 1. This cartridge holder assembly 10 of a drug delivery device comprises a cartridge holder 14 adapted to receive a cartridge 12, which is hermetically sealed with a flexible and deformable septum 22. At its lower and distal end section, the cartridge holder 14 is threadedly engaged with a needle mount 16. Said mount or needle holder 16 comprises a threaded cylindrical portion allowing to screw the needle holder 16 on the threaded neck portion of the cartridge holder 14. At its lower and distal section, the mount 16 comprises a flange-like bottom face 17, which in a concentrically inner section holds the injection needle or cannula 20.

During assembly of the needle holder 16, the proximally located tipped end of the needle 20 penetrates the septum 22. In this way, a fluid-transferring connection for the purpose of dose dispensing can be established. Additionally, the distal and free end of the needle 20 can be provided with a replaceable needle cap 19. Also, the entire cartridge holder assembly 10 can be covered and protected by a protective cap 18.

Depending on manufacturing tolerances and the corresponding design of cartridge 12 and cartridge holder 14, an axial gap 24 of variable size is typically formed between the bottom portion 17 of the needle holder 16 and the distal end face of the cartridge 16. Axial size of this free space area 24 may vary, e.g due to manufacturing and assembly tolerances. In particular, during dispensing of a dose of the medicinal fluid contained in the cartridge 12, a respective fluid pressure is built-up, which, due to the elasticity of the septum 22, leads to a respective axial expansion of the septum 22. As a consequence, the septum 22 may almost entirely fill said free space area 24 when a respective fluid pressure inside the cartridge 12 establishes.

Due to the elastic properties of the septum 22, said septum 22 will store elastic energy during dose dispensing. But as soon as the fluid pressure returns to an initial value after a dose dispensing procedure, the septum 22 relaxes to its initial configuration, which is accompanied by a retraction of the expanded section of the septum 22 into the cartridge 12. However, also such a retracting motion may in turn lead to a built-up of a non-negligible fluid pressure enhancement and, as a consequence, a certain amount of medicinal fluid may be supplementally expelled from the cartridge 12, which can be typically observed in the form of droplet formation at the distal tip of the needle 20.

OBJECTS OF THE INVENTION

It is therefore an object of the present invention, to provide an improved cartridge holder assembly for a drug delivery device, which counteracts generation of droplets after termination of a dose dispensing procedure. It is a further object of the invention, to provide an effective means adapted to prevent septum deformation during dose dispensing. Furthermore, the invention focuses on an inexpensive as well as stable and robust design of a drug delivery device.

SUMMARY OF THE INVENTION

The present invention provides a cartridge holder assembly for a drug delivery device for dispensing of a dose of a medicinal product. The cartridge holder assembly comprises a cartridge holder, which is adapted to receive a cartridge. The cartridge, typically designed as vial, carpule or ampoule is filled or is to be filled with a medicinal product to be dispensed by the drug delivery device in a well-defined way, typically in multiple doses.

The cartridge typically containing heparin or insulin is hermetically sealed by means of a flexible and deformable septum, which is penetrable by a piercing element, such as an injection needle or cannula. The cartridge holder further comprises at least a through opening at a distal end section to receive the piercing element to be coupled with the inside volume of the cartridge in a fluid-transferring way.

The cartridge holder assembly further comprises a constriction member, which is adapted to flexibly abut axially against the septum of the cartridge. The constriction member also comprises a through opening to receive the piercing element. The constriction member provides axial support for the cartridge's distal end section and in particular for the septum of the cartridge. By providing axial abutment, the constriction member may effectively prevent or counteract a distally directed axial expansion of the septum during a dose dispensing procedure.

Further, the through opening of the constriction member is adjustable in diameter. In this way, the constriction member can be universally adapted to compensate for a large range of manufacturing and assembly tolerances.

By way of the deformable constriction member, the volume and size of a septum extension area can be reduced advantageously, thus preventing the unintentional axial expansion of the septum under dose dispensing conditions. In this way, also the magnitude and impact of a subsequent elastic relaxation process of the septum can be advantageously reduced providing a respective reduction of the generation of droplets.

According to a first preferred embodiment of the invention, the axial position of the through opening of the constriction member is adjustable. In this way, the constriction member provides a kind of abutment piece, which is universally able to compensate for manufacturing and assembly tolerances. Irrespective of the initial size of a septum extension area as defined by an axial gap between a mount of a piercing element and the distal end face of the cartridge, the constriction member serves as a flexible and universally adaptable strut counteracting an axial and distal expansion of the cartridge's septum.

According to a further preferred embodiment, the constriction member comprises numerous retention elements. The retention elements are preferably axially and/or radially displaceable. Alternative or additionally, these retention elements are pivot-mounted axially and/or radially. By means of the displaceable or pivotable retention elements, the constriction member allows for a flexible compensation of tolerances.

In a further embodiment, the constriction member is designed as insert piece to be axially displaced between the septum of a cartridge and a piercing element's mount. Typically, the constriction member might become subject to an elastic or plastic deformation during assembly of the piercing element's mount with the cartridge holder.

By designing the constriction member as a separate piece to be placed between septum and mount of a piercing element, even existing cartridge holder assemblies might be retrofitted with said constriction member.

In a further alternative embodiment, the constriction member is integrally formed with the cartridge holder. Constriction member and cartridge holder are for instance designed as a single plastic component manufactured by injection molding. Typically, the constriction member is disposed at the cartridge holder's distal end section. It may serve as distal end face or bottom of the cartridge holder.

In a further preferred embodiment, the constriction member is of substantially circular disc-shaped geometry. Furthermore, it comprises radially extending slits or gaps between its various retention elements. By means of these radial slits or gaps, the various retention elements can be moved or pivoted in axial direction.

According to a further preferred embodiment, the retention elements of the constriction member comprise a circular segment shape. Further, they are pivot mounted at an outer annular edge of the constriction member. In embodiments, where the constriction member and the cartridge holder are formed as a unitary piece, the retention elements may also pivoted at a wall section of the cartridge holder. Said retention elements may further comprise a flap-like shape.

In an initial, pre-assembly configuration, said retention elements may point with a radially inwardly protruding end or tip in distal direction, i.e. away from the septum of the cartridge. However, during assembly of the mount of the piercing element, said mount will get in contact with the tips of the retention elements and as the mount is further displaced in proximal direction, until it reaches its finally assembly position, the flap-like retention elements are pivoted in proximal direction, thus reducing the septum extension area otherwise filled by the septum during dose dispensing.

According to a further preferred embodiment, the retention elements are coupled to an outer edge or outer frame of the constriction member by means of flexible deformable coupling elements. In embodiments, where cartridge holder and constriction member are integrally formed, said outer edge or outer frame is preferably designed as an integral part of the cartridge holder.

Typically, the flexible deformable coupling elements at least slightly protrude in distal direction. Upon assembly of the piercing element's mount, they become deformed in a well-defined way leading to a radially inwardly directed displacement of the constriction member, which in turn reduces the size of the septum extension area in radial direction.

Generally, according to a further embodiment of the invention, the constriction member's through opening reduces in diameter in response of an axially and/or proximally directed displacement of the retention elements and/or the coupling elements. Additionally or alternatively, the constriction member's through opening reduces in diameter in response of an axially and/or proximally directed deformation, either elastic or plastic deformation of the retention elements and/or the coupling elements.

In a further preferred embodiment of the invention, the coupling elements in an initial configuration, comprise a U- or V-shaped distally extended groove. In this way, during assembly of the piercing element's mount, said flange-like mount abuts against these coupling elements leading to a respective deformation of the coupling elements in proximal direction, which as a consequence, leads to a radially inwardly directed displacement of the retention elements operably engaged with the coupling elements.

Accordingly, the retention elements of the constriction members experience a radially inwardly directed displacement in response of an axially and proximally directed displacement of their corresponding coupling elements. In this way, the through opening of the constriction member can be advantageously reduced in size during and by an assembly of the piercing element's mount with the cartridge holder.

According to another independent aspect, the invention also provides a drug delivery device for dispensing of a dose of a medicinal product. Said drug delivery device comprises a cartridge filled with or to be filled with the medicinal product to be dispensed. The drug delivery device further comprises a drive mechanism, which is operably engaged with the cartridge for dispensing of a predefined dose of the medicinal product. Further, the drug delivery device is characterized by a cartridge holder assembly as described above.

In another but further independent aspect, the invention also provides a method of assembly of a drug delivery device that comprises a cartridge, a drive mechanism and a cartridge holder assembly as described above. The method characterizes by an assembly procedure for connecting the piercing element with the housing or with a cartridge holder of said drug delivery device. During assembly of a piercing element, the mount of the piercing element is shifted against the constriction member in proximal direction. This proximally directed displacement then in response reduces the diameter of the through opening of the constricting member. Additionally and/or alternatively, by the piercing element-induced deformation or displacement of the constriction member and/or its retention elements, a distally directed expansion of the cartridge's sealing septum can be effectively prevented or at least counteracted.

The term "medicament", or "medicinal product" as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

Without limitation, the present invention will be explained in greater detail below in connection with preferred embodiments and with reference to the drawings in which.

DETAILED DESCRIPTION

Figure 1:
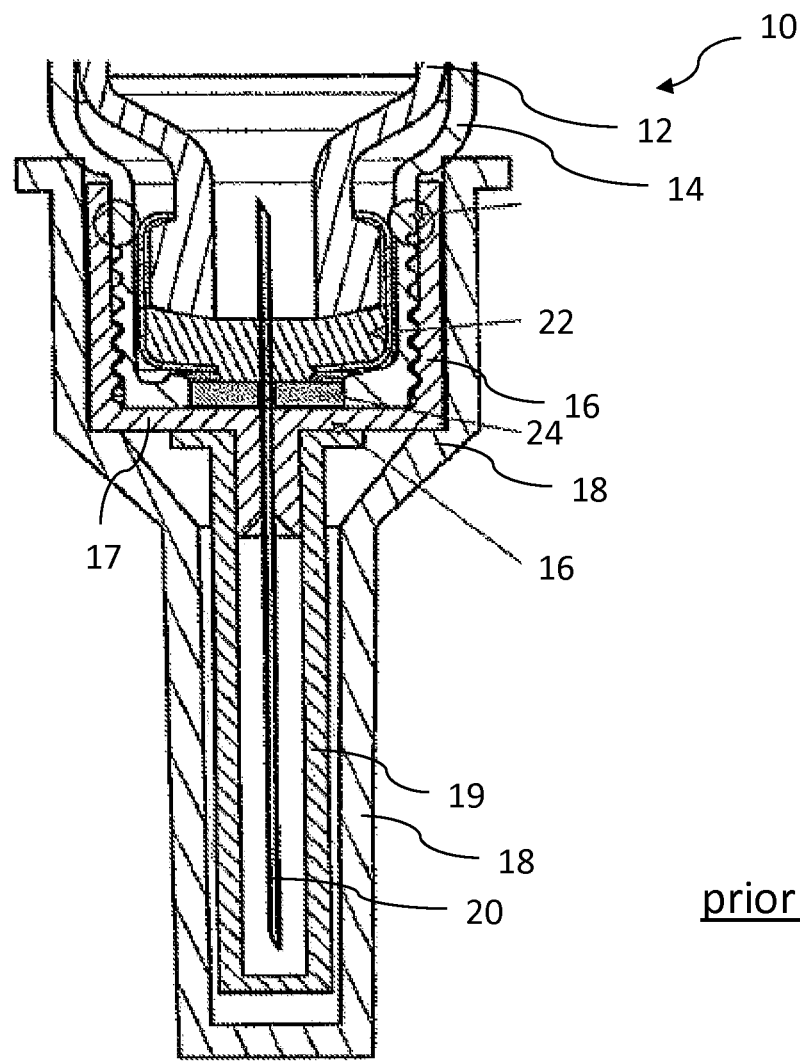
FIG. 1 schematically illustrate a cartridge holder assembly in cross-sectional view according to the prior art.

In FIGS. 2 to 5, a first embodiment of the constriction member 26 is shown. The constriction member 26 comprises three retention elements 28, 30, 32 of circular segment shape. The retention elements 28, 30, 32 are separated by radially extending slits or gaps 29, 31, 33. Further, the retention elements 28, 30, 32 are pivot mounted at their outer annular edge 27. In this way, the entire constriction member 26 may comprise a shape with variable height in axial direction. As the orientation of the various retention elements 28, 30, 32 varies, also the size of its concentric through opening 34 formed by the retention elements 28, 30, 32 changes accordingly.

Figure 2:
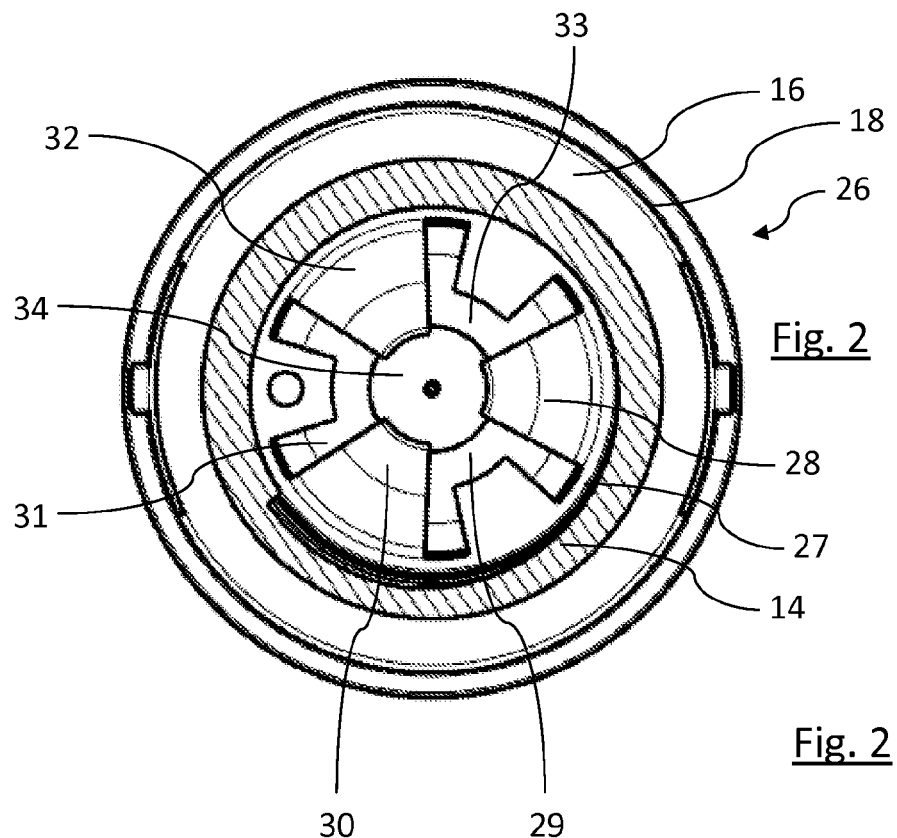
FIG. 2 shows a cross sectional view of the cartridge holder assembly according to a first embodiment of the invention.
Figure 3:
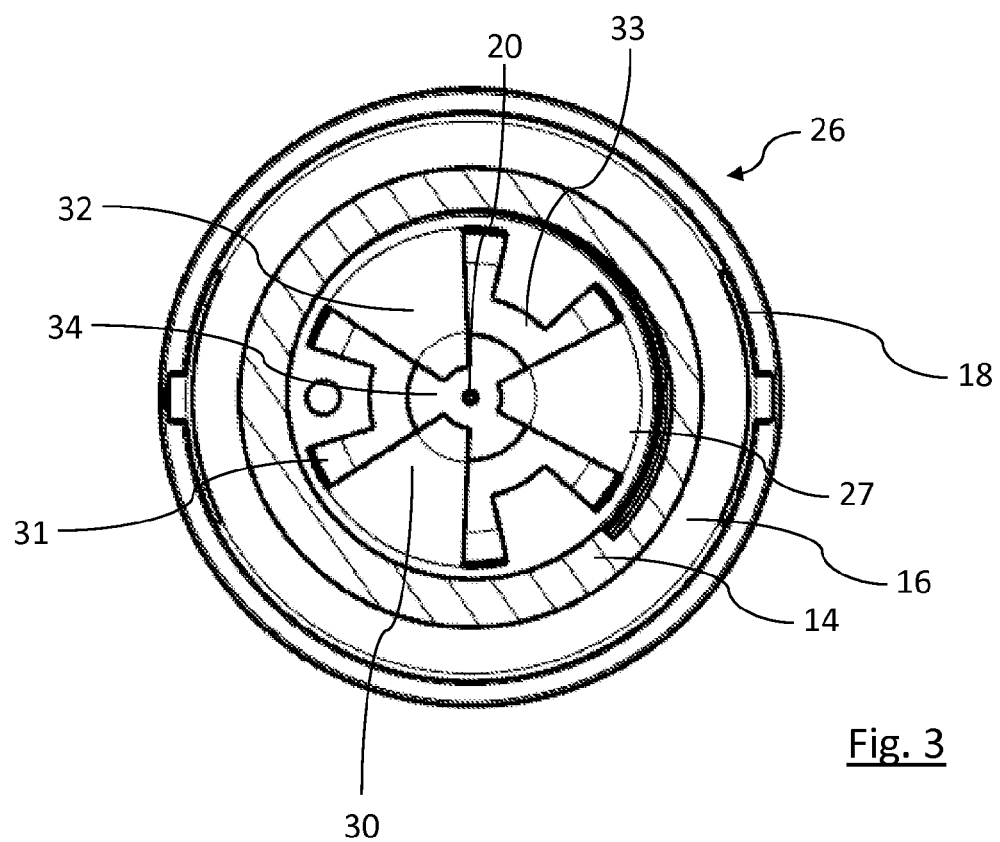
FIG. 3 illustrates a cross sectional view of the assembly according to FIG. 2 in a constricted configuration.
Figure 4:
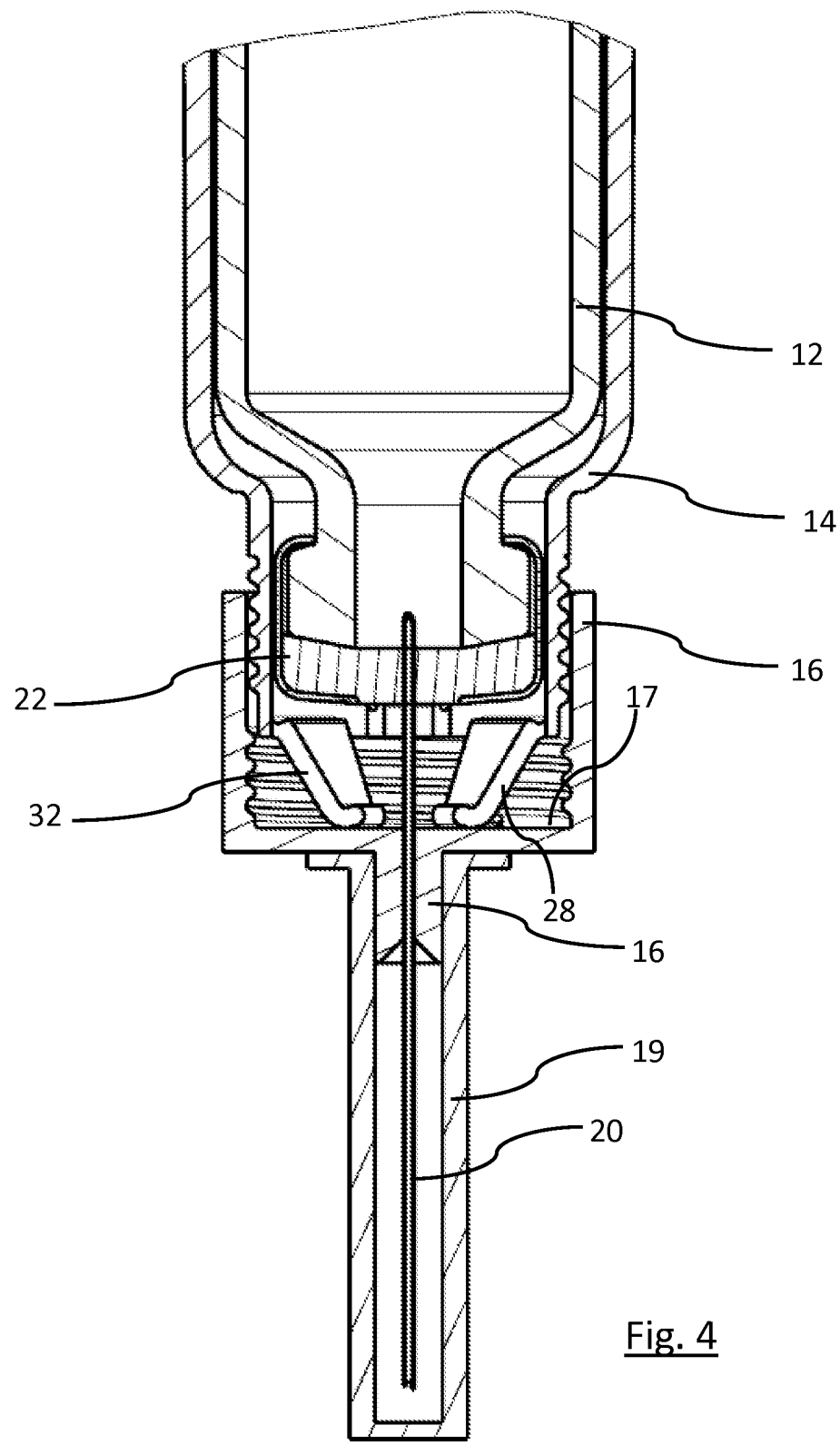
FIG. 4 shows a cross sectional illustration along the longitudinal axis of the cartridge holder assembly according to the configuration of FIG. 2.

In FIGS. 2 and 4, the constriction member 26 is illustrated in an initial configuration, in which the holder 16 of the needle 20 has not yet been disposed in its final assembly position at the cartridge holder 14. The retention elements 28, 30, 32 point radially inwardly, in distal, hence downward direction. Further, by way of displacing the needle holder 16 in proximal direction, its flange-like portion 17 abuts against the free ends of the retention elements 28, 30, 32. Any further proximally directed displacement of the needle holder 16 then leads to an inwardly directed pivoting of the various retention elements 28, 30, 32, finally leading to the reduced septum extension area.

Figure 5:
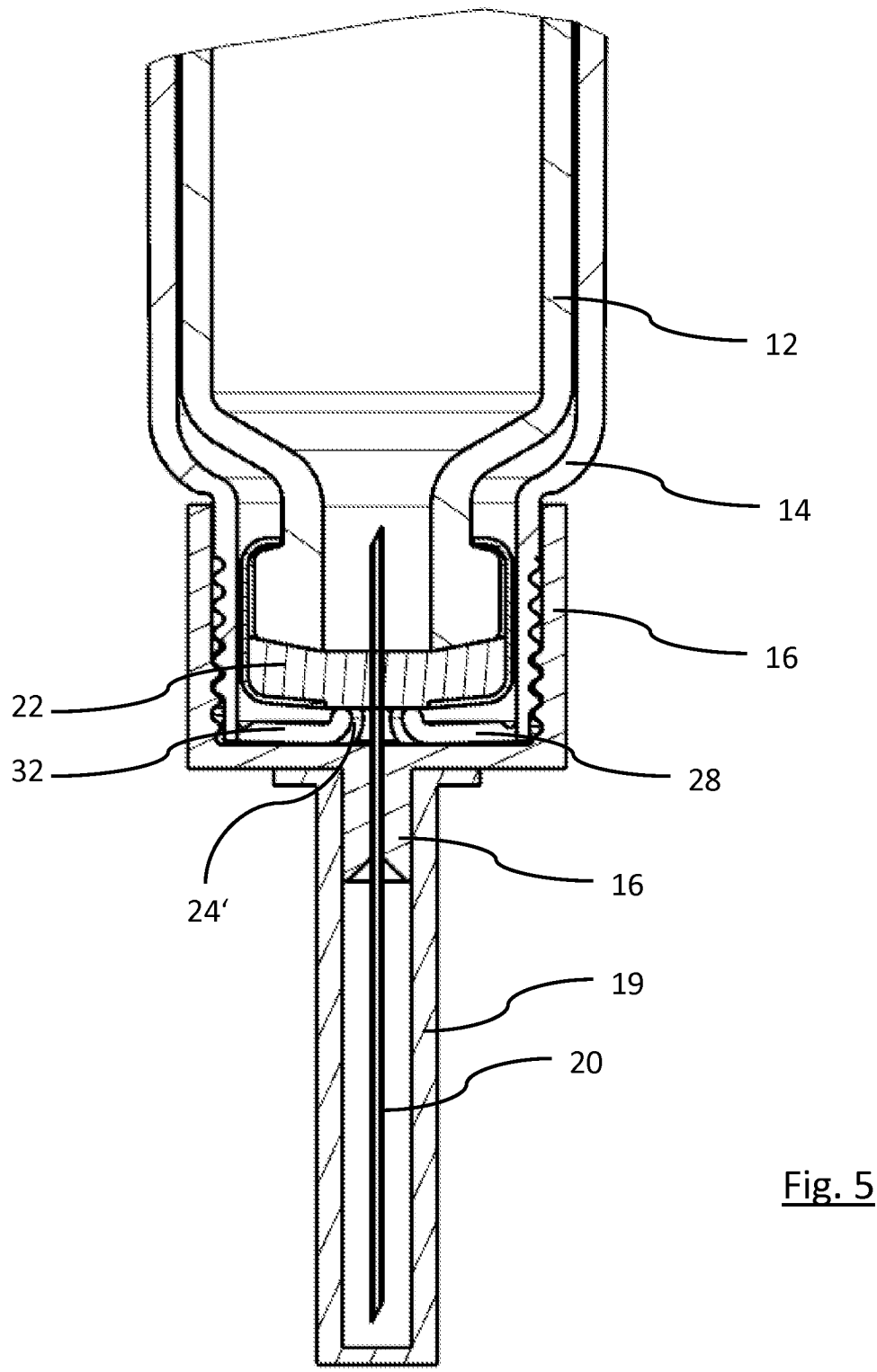
FIG. 5 shows a cross sectional illustration along the longitudinal axis of the cartridge holder assembly according to the configuration of FIG. 3, FIG. 6 illustrated a longitudinal cross section of another embodiment of the cartridge holder assembly in initial configuration.

By means of the flap-like and pivot-mounted retention elements 28, 30, 32, the former septum extension area 24 as illustrated in FIG. 1 can be reduced in size to a septum extension area 24' as illustrated in FIG. 5. In fact, the retention elements 28, 30, 32 become flattened and sandwiched between the bottom face 17 of the needle holder 16 and a distal end face of the cartridge 12.

Consequently, during dose injection, the septum 22 is restricted and can no longer extend and expand into the former septum extension area. In this way, elastic post-dispensing relaxation of the septum 22 can be circumvented and the generation of droplets can be effectively reduced.

Figure 6:
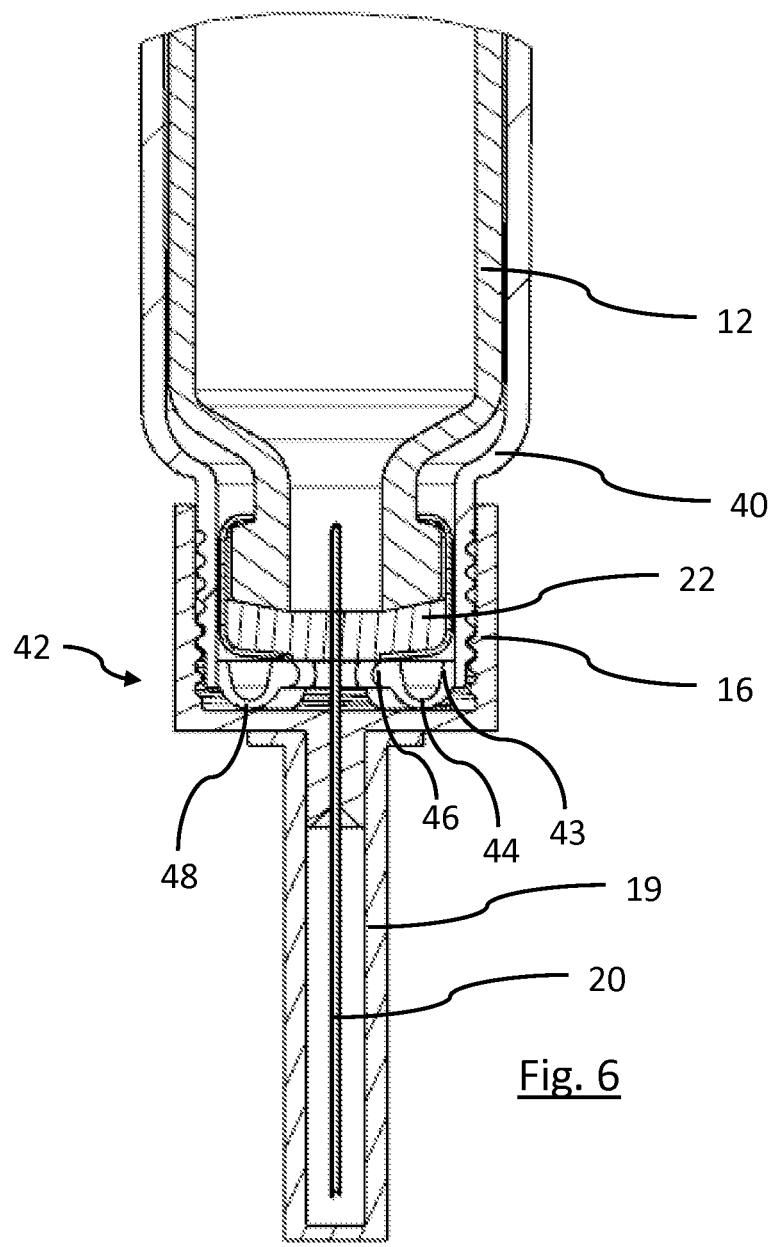
Figure 7:
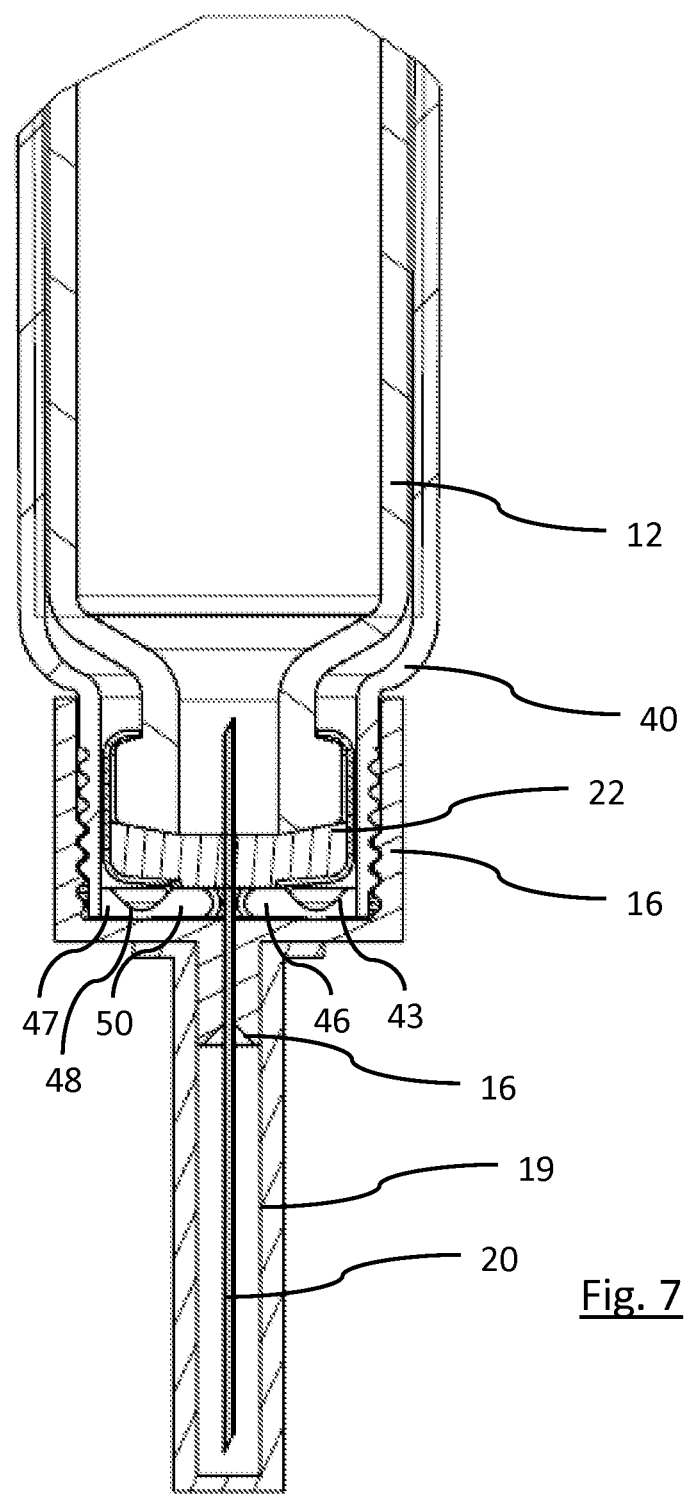
FIG. 7 illustrates the constriction member according to FIG. 6 in final assembly configuration.
Figure 8:
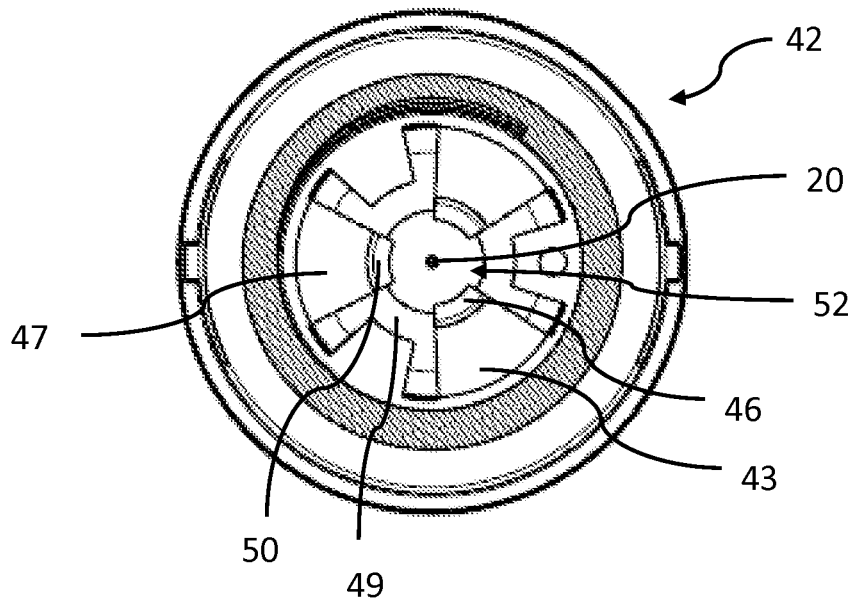
FIG. 8 shows a lateral cross section according to the embodiment of FIG. 6
Figure 9:
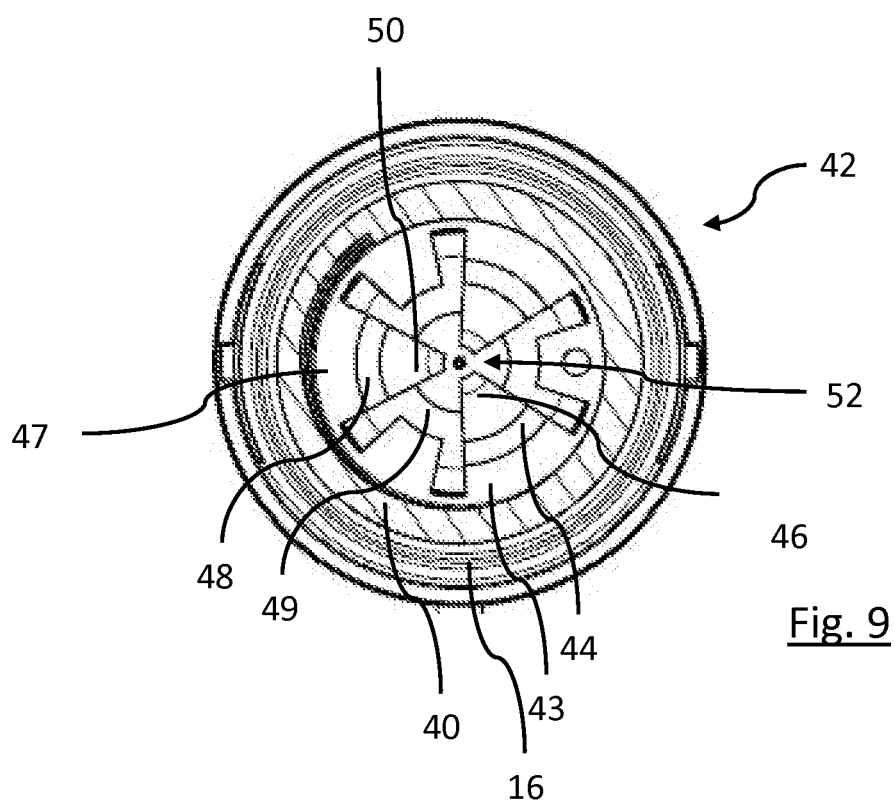
FIG. 9 shows a lateral cross section according to the embodiment of FIG. 7.

In FIGS. 6 through 9 another embodiment of the constriction member 42 is illustrated. Also here, various retention elements 46, 50 as illustrated in FIGS. 8 and 9 are separated by a radial slits 49. The constriction member 42 and its retention elements 46, 50 substantially entirely extend in a plane perpendicular to the axial elongation of the cartridge 12 and/or the drug delivery device. Further, the retention elements 46, 50 are arranged in a substantially radially sliding displaceable way.

The retention elements 46, 50 also comprise a substantially circular segment shape. In contrast to the embodiment as illustrated in FIGS. 2 to 5, the retention elements 46, 50 are flexibly coupled and engaged with annular frame portions 43, 47 or respective outer edges of the constriction member 42.

The flexible coupling is provided by interjacent coupling elements 44, 48, which comprise a U- or V-shaped distally extended groove as illustrated in FIG. 6. In the illustrated embodiment, the constriction member 42 is integrally formed with the sidewall of the cartridge holder 40. Also here, the constriction member 42 may be designed as a separate piece to be sandwiched between cartridge 12 and flange-like portion 17 of the needle holder 16.

In the illustration according to FIG. 8, which corresponds to the longitudinal cross sectional illustration according to FIG. 6, the constriction member 42 comprises a rather large through opening 52 in its initial configuration. As soon as the needle holder 16 is assembled with the cartridge holder 14, the radially extending flange portion 17 of the needle holder 16 exerts axial and proximally directed thrust to the distally protruding coupling elements 44, 48. Due to their elasticity, the coupling elements 44, 48 flatten and slidingly displace the corresponding retention elements 46, 50 radially inwardly in order to reduce the diameter of the through opening 52.

The constriction member 42 may comprise a plurality of different components and elements. For instance, the radially outwardly disposed annular frame portion 43 as well as the radially inwardly arranged retention elements 46, 50 may comprise a comparatively hard and inelastic plastic component, whereas the coupling elements 44, 48 may comprise a relatively soft and elastic material. The constriction member 42 can for instance be manufactured as two- or more component injection molded piece. Alternatively, it is conceivable, that the various components of the constriction member 42, in particular its retention elements 46, 50 and coupling elements 44, 48 as well as the outer frame 43 are integrally formed as a single piece, which might be an integral portion of the cartridge holder 14. When designed as a single piece, the coupling elements or flexible coupling portions 44, 48 of the constriction member 42 may feature a smaller axial thickness compared to the adjacently disposed constriction elements 46, 50 and/or the outer frame portions 43, 47. In this way a required elasticity of the coupling elements 44, 48 can be provided.

Consequently, as illustrated in FIG. 7, the former septum extension area is reduced in size compared to the initial configuration as illustrated in FIG. 6. In this way, unintentional distally directed extension of the cartridge's 12 septum 22 can be effectively counteracted or can even entirely be prevented.

REFERENCE NUMERALS 10 cartridge holder assembly
12 cartridge
14 cartridge holder
16 needle holder
17 flange portion
18 protection cap
19 needle cap
20 needle
22 septum
24 septum extension area
26 constriction member
28 retention element
29 slit
30 retention element
31 slit
32 retention element
33 slit
34 through opening
40 cartridge holder
42 constriction member
43 frame portion
44 coupling element
46 retention element
47 frame portion
48 coupling element
49 slit
50 retention element
52 through opening

The invention claimed is:

1. Cartridge holder assembly for a drug delivery device comprising:
 a cartridge holder adapted to receive a cartridge to be filled with a medicinal product to be dispensed by the drug delivery device, wherein the cartridge holder comprises at least one through opening at a distal end section to receive a piercing element being adapted to penetrate a sealing septum of the cartridge,
 a constriction member comprising one or more displaceable and/or pivotable retention elements and adapted to axially abut against the septum and form a through opening to receive the piercing element, wherein said through opening is adjustable in diameter.

2. The cartridge holder assembly according to claim 1, wherein the axial position of the through opening of the constriction member is adjustable.

3. The cartridge holder assembly according to claim 1, wherein the constriction member is designed as insert piece to be axially placed between the septum of the cartridge and a piercing element's mount.

4. The cartridge holder assembly according to claim 1, wherein the constriction member is integrally formed with the cartridge holder and wherein the constriction member is disposed at the cartridge holder's distal end section.

5. The cartridge holder assembly according to claim 1, wherein the constriction member is of circular disc-shaped geometry and comprises radially extending slits or gaps between retention elements.

6. The cartridge holder assembly according to claim 1, wherein the retention elements comprise a circular segment shape and are pivot mounted at their outer edge.

7. The cartridge holder according to claim 1, wherein the retention elements are coupled to an outer edge or outer frame of the constriction member by means of flexible deformable coupling elements.

8. The cartridge holder assembly according to claim 1, wherein the constriction member's through opening reduces in diameter in response of an axially and/or proximally directed displacement and/or deformation of the retention elements and/or the coupling elements.

9. The cartridge holder assembly according to claim 8, wherein in an initial configuration, the coupling elements form a U- or V-shaped distally extended groove.

10. The cartridge holder assembly according to claim 9, wherein the retention elements experience a radially inwardly directed displacement in response of an axially proximally directed displacement of the corresponding coupling elements.

11. A drug delivery device for dispensing of a dose of a medicinal product, comprising:
 a cartridge filled with the medicinal product,
 drive mechanism operably engaged with the cartridge to dispense a predefined dose of the medicinal product,
 a cartridge holder assembly according to claim 1.

12. A method of assembly of a drug delivery device comprising a cartridge, a drive mechanism and a cartridge holder assembly according to claim 1, wherein during assembly of a piercing element, the mount of the piercing element is shifted against the constriction member in proximal direction, which in response reduces the diameter of its through opening.

* * * * *